United States Patent [19]

Merce-Vidal et al.

[11] Patent Number: 5,227,486

[45] Date of Patent: Jul. 13, 1993

[54] PROCESS FOR THE PREPARATION OF ARYL (OR HETEROARYL) PIPERAZINYLBUTYLAZOLE DERIVATIVES

[75] Inventors: Ramon Merce-Vidal; Jordi Frigola-Constansa; Juan Pares-Corominas, all of Barcelona, Spain

[73] Assignee: Laboratorios Del Dr. Esteve, S.A., Barcelona, Spain

[21] Appl. No.: 847,625

[22] Filed: Mar. 6, 1992

[30] Foreign Application Priority Data

Mar. 7, 1991 [FR] France ............... 91 02735

[51] Int. Cl.$^5$ ............... C07D 403/14; C07D 471/04; C07D 417/14
[52] U.S. Cl. ............... 544/295; 544/362; 544/366; 544/368; 544/370; 544/371; 544/372; 544/373
[58] Field of Search ............... 544/295, 366, 362, 368, 544/370, 371, 372, 373

[56] References Cited

U.S. PATENT DOCUMENTS 5,128,343 7/1992 Pinol et al. ............... 544/295

OTHER PUBLICATIONS

Chemical Abstracts, vol. 115, No. 17, Oct. 1991; Malinka "Synthesis and 2H-2(4-substituted-1-piperazinylalkyl)-4,6-dimethyl-3-oxo-2,-3-dihydroisothiazolo(5,4-b)pyridines" & Acta Pol. Pharm. 1990, vol. 47, Nos. 1-2 CA 115:183160n.
Chemical Abstracts, vol. 70, No. 13, Nov. 31, 1969; Stogryn "Antimalarials related to 2-bromo-4,5-dimethoxy-N,N-bis(diethylaminoethyl)aniline" & J. Med. Chem. 1969, vol. 12, No. 1 CA 70:57766d.

*Primary Examiner*—Patricia L. Morris
*Attorney, Agent, or Firm*—Dressler, Goldsmith, Shore, Sutker & Milnamow, Ltd.

[57] ABSTRACT

The present invention relates to a process for the preparation of aryl (or heteroaryl) piperazinyl-butylazole derivatives corresponding to the general formula I

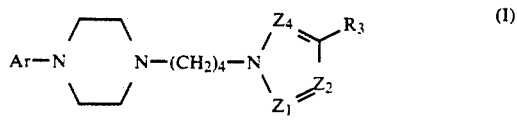

in which
Ar denotes a nitrogenous or other aromatic radical chosen from differently substituted aryls, differently substituted 2-pyrimidine, 2-N-methyl-imidazole and 3-(1,2-benzisothiazole)
$Z_1$ denotes a nitrogen atom or an optionally substituted carbon atom which may be denoted by: C-$R_1$
$Z_2$ denotes a nitrogen atom or an optionally substituted carbon atom which may be denoted by: C-$R_2$
$Z_4$ denotes a nitrogen atom or an optionally substituted carbon atom which may be denoted by: C-$R_4$ and $R_1$, $R_2$, $R_3$ and $R_4$, which are identical or different and may also form a part of another ring, aromatic or otherwise, denote a hydrogen atom, a halogen, a lower alkyl radical, a nitro radical, a hydroxyl radical, an alkoxy radical, a cyano radical, a carboxylic radical, a carboxamido radical, an alkylcarboxylate radical, an aryl or substituted aryl radical, a sulfonic radical, a sulfonamido radical optionally substituted on the amino group or an amino or substituted amino radical wherein

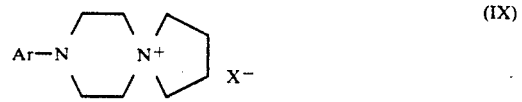

in which
Ar has the meanings referred to above and X denotes a halogen atom, is reacted with a compound of general formula III

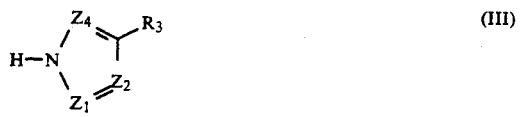

in which
$Z_1$, $Z_2$, $Z_4$ and $R_3$ have the meanings referred to above.

11 Claims, No Drawings

PROCESS FOR THE PREPARATION OF ARYL (OR HETEROARYL) PIPERAZINYLBUTYLAZOLE DERIVATIVES

The present invention relates to a process for the preparation of aryl (or heteroaryl) piperazinylbutylazole derivatives, which is endowed with an excellent yield (higher than 80%) and which results in very pure products. These derivatives correspond to the general formula I

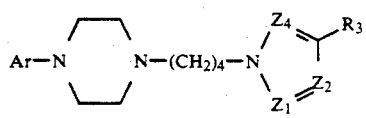

in which
$Z_1$ denotes a nitrogen atom or an optionally substituted carbon atom which may be denoted by: $C-R_1$
$Z_2$ denotes a nitrogen atom or an optionally substituted carbon atom which may be denoted by: $C-R_2$
$Z_4$ denotes a nitrogen atom or an optionally substituted carbon atom which may be denoted by: $C-R_4$ and $R_1$, $R_2$, $R_3$ and $R_4$, which are identical or different and may also form a part of another ring, aromatic or otherwise, denote a hydrogen atom, a halogen, a lower alkyl radical, a nitro radical, a hydroxyl radical, an alkoxy radical, a cyano radical, a carboxylic radical, a carboxamido radical, an alkylcarboxylate radical, an aryl or substituted aryl radical, a sulfonic radical, a sulfonamido radical optionally substituted on the amino group or an amino or substituted amino radical.

The 1-{4-[4-[aryl (or heteroaryl)]-1-piperazinyl]-butyl}-1H-azole derivatives of general formula I are agents with pharmacological activity on the central nervous system; in particular they exhibit anxiolytic and tranquilizing, as well as antidepressant, activities in the inhibition of the abstinence syndrome and in the disorders associated with cognition and on the cardiovascular system in particular with antihypertensive activity, described in our own work (U.S. Pat. No. 5,162,323 and U.S. patent application Ser. No. 07/326,929).

In the previous techniques cited above the 1-{4[4-[aryl (or heteroaryl)]-1-piperazinyl]butyl}-1H-azole derivatives were prepared by means of one of the following methods:

By reaction of a compound of the general formula

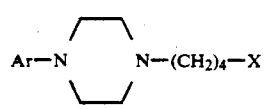

in which
Ar has the meanings referred to above and X denotes a halogen atom or a leaving group chosen from tosyloxy or mesiloxy, with a compound of general formula III

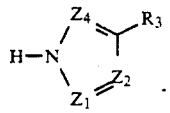

in which
$A_1$, $Z_2$, $Z_4$ and $R_3$ have the meanings referred to above, or else by reaction of a compound of general formula IV

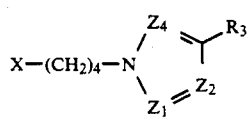

in which
$Z_1$, $Z_2$, $Z_4$, $R_3$ and X have the meanings referred to above, with a compound of general formula V

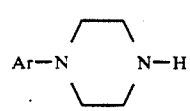

in which
Ar has the meanings referred to above, or by reaction of a compound of general formula VI

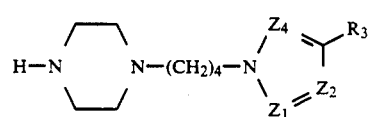

in which
$Z_1$, $Z_2$, $Z_4$ and $R_3$ have the meanings referred to above, with a compound of general formula VII.

$$Ar-X \quad\quad (VII)$$

in which
Ar and X have the meanings referred to above, or else by reaction of a compound of general formula VIII

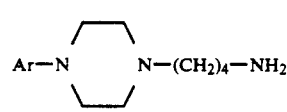

in which
Ar has the meanings referred to above, with 2,5-dimethoxytetrahydrofuran.

The present invention relates to a new process for the preparation of derivatives of general formula I as defined above, which permits the improvement in the yields in which these products are obtained and the industrial implementation. In accordance with the invention the derivatives of general formula I are prepared by reacting a compound of general formula IX

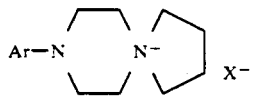

(IX)

in which
Ar and X have the meanings referred to above with a compound of general formula III

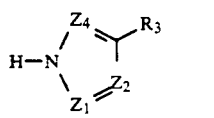

(III)

in which
$Z_1$, $Z_2$, $Z_4$, $R_1$, $R_2$, $R_3$ and $R_4$ have the meanings referred to above.

The reaction between the compounds of general formulae IX and III takes place in a suitable solvent, for example dimethyl sulfoxide, dimethylformamide, an alcohol such as ethanol or any one of the propanols or butanols, a hydrocarbon, aromatic or otherwise, such as heptane, benzene or toluene, an ether such as dioxane or diphenyl ether or a mixture of these solvents; dimethylformamide is preferably employed. This reaction is advantageously conducted in the presence of an inorganic base such as alkali metal hydroxides, carbonates or bicarbonates or else a mixture of these bases, as well as of an organic base such as pyridine, triethylamine or potassium tert-butoxide; potassium carbonate is preferably employed.

The most suitable temperatures vary between room temperature and the reflux temperature of the solvent, preferably between 80° C. and 160° C., and the reaction time is between 1 hour and 24 hours.

By proceeding in this manner, derivatives of general formula I which have a very high degree of purity are obtained in accordance with the present invention. These derivatives are furthermore obtained by a process for industrial application which is very simple and which results in a very high yield.

The starting materials of general formula IX are prepared according to the methods described, for example: Yevich J. P. et al., *J. Med. Chem.*, 1986, 29, 359.

A large number of compounds have been prepared by the process of the invention. Their physicochemical data have been assembled in Tables I to III. The preparation of some derivatives of general formula I has been described in detail below.

EXAMPLE 11

Preparation of 4,5-dichloro-2-methyl-1-(4-[4-(2-pyrimidinyl)-1-piperazinyl]butyl)-1H-imidazole A mixture of 450 g (1.5 moles) of 8-(2-pyrimidinyl)-8-aza-5-azoniaspiro[4,5]decane bromide, 225 g (1.5 moles) of 4.5-dichloro-2-methylimidazole and 300 g (2.25 moles) of potassium carbonate in 2 l of dimethylformamide is heated to 130°-135° for 14 hours. The mixture is evaporated under vacuum, chloroform is added, the solution is washed with water, dried over sodium sulfate and evaporated under vacuum, and 503 g (91%) of 4,5-dichloro-2-methyl-1-{4-[4-(2-pyrimidinyl)-1-piperazinyl]butyl}-1H-imidazole are obtained in liquid form.

The spectroscopic data for the identification of this product are set out in Table I.

EXAMPLE 16

Preparation of 1-{4-[4-(2-pyrimidinyl)-1-piperazinyl]butyl}-1H-benzimidazole.

A mixture of 450 g (1.50 moles) of 8-(2-pyrimidinyl)-8-aza-5-azoniaspiro[4,5]decane bromide, 177 g (1.50 moles) of benzimidazole and 307 g (2.25 moles) of potassium carbonate in 2 l of dimethylformamide is heated to 140°-145° C. for 14 hours. The mixture is evaporated under vacuum, chloroform is added, the solution is washed with water, dried over sodium sulfate and evaporated under vacuum, and 457 g (91%) of 1-{4-[4-(2-pyrimidinyl)-1-piperazinyl]butyl}-1H-benzimidazole, with a melting point of 85°-88° C., are obtained.

The spectroscopic data for the identification of this product are set out in Table I.

EXAMPLE 27

Preparation of 1-{4-[4-(2-pyrimidinyl)-1-piperazinyl]butyl}-1H-pyrazole.

A mixture of 730 g (3.59 moles) of 8-(2-pyrimidinyl)-8-aza-5-azoniaspiro[4,5]decane bromide, 275 g (4.05 moles) of pyrazole and 745 g (5.4 moles) of potassium carbonate in 3 l of dimethylformamide is heated to 140° C. for 14 hours. The mixture is evaporated under vacuum, chloroform is added, the solution is washed with water, dried over sodium sulfate and evaporated under vacuum, and 650 g (94%) of 1-{4-[4-(2-pyrimidinyl)-1-piperazinyl]butyl}-1H-pyrazole are obtained in liquid form.

The spectroscopic data for the identification of this product are set out in Table I.

EXAMPLE 34

Preparation of 4-chloro-1-{4-4-(2-pyrimidinyl)-1-piperazinyl]butyl}-1H-pyrazole

A mixture of 8.5 kg (28.41 moles) of 8-(2-pyrimidinyl)-8-aza-5-azoniaspiro[4,5]decane bromide, 3.5 kg (34.14 moles) of 4-chloropyrazole and 5.5 kg (39.8 moles) of potassium carbonate in 25.5 l of dimethylformamide is heated to 120°-125° C. for 22 hours. The mixture is evaporated under vacuum, chloroform is added, the solution is washed with water, dried over sodium sulfate and evaporated under vacuum, and 7.94 kg (87%) of 4-chloro-1-{4-[4-(2-pyrimidinyl)-1-piperazinyl]butyl}-1H-pyrazole are obtained in liquid form.

The spectroscopic data for the identification of this product are set out in Table I.

EXAMPLE 77

Preparation of 4,5-dichloro-2-methyl-1-{4-4-(2-methoxyphenyl)-1-piperazinyl]butyl}-1H-imidazole A mixture of 130 g (0.4 moles) of 8-(2-methoxyphenyl)-8-aza-5-azoniaspiro[4,5]decane bromide, 66 g (0.44 moles) of 4,5-dichloro-2-methylimidazole and 8.2 g (0.6 moles) of potassium carbonate in 700 ml of dimethylformamide is heated to 130° C. for 20 hours. The mixture is evaporated under vacuum, chloroform is added, the solution is washed with water, dried over sodium sulfate and evaporated under vacuum, and 130 g (82%) of 4,5-dichloro-2-methyl-1-{4-[4-(2-methoxyphenyl)-1-piperazinyl]butyl}-1H-imidazole, with a melting point of 82°–83° C., are obtained.

The spectroscopic data for the identification of this product are set out in Table II.

EXAMPLE 88

Preparation of 4-chloro-1-{4-4-(3-(1,2-benzisothiazolyl))-1-piperazinyl}butyl}-1H-pyrazole.

A mixture of 67 g (0.19 moles) of 8-(1,2-benzisothiazol-3-yl)-8-aza-5-azoniaspiro[4,5]decane bromide, 20.5 g (0.2 moles) of 4-chloropyrazole and 41 g (0.3 moles) of potassium carbonate in 300 ml of dimethylformamide is heated to 140° C. for 18 hours. The mixture is evaporated under vacuum, chloroform is added, the solution is washed with water, dried over sodium sulfate and evaporated under vacuum, and 60 g (80%) of 4-chloro-1-{4-[4-(3-(1,2-benzisothiazolyl))-1-piperazinyl]butyl}-1H-pyrazole are obtained in liquid form.

The spectroscopic data for the identification of this product are set out in Table III.

TABLE I

[Structure: piperidine-pyrimidine compound with N—(CH₂)₄—N linker to a ring bearing $Z_1$, $Z_2$, $Z_4$, $R_1$, $R_3$]

| Example | $Z_1$ | $Z_2$ | $Z_4$ | $R_3$ | M.P. | IR cm$^{-1}$ | NMR solvent | $^1$H-NMR (100 MHz), δ, J=Hz |
|---|---|---|---|---|---|---|---|---|
| 1 | CH | CH | CH | H | Oil | 2941, 1585, 1547, 1500, 1360, 1260, 983, 724 (film) | CDCl$_3$ | 1.55(m, 2H); 1.77(m, 2H); 2.25–2.55(a.c. 6H); 3.70–4.05 (a.c. 6H); 6.13(t, J=2.0Hz, 2H); 6.47(t, J=4.7Hz, 1H); 6.65 (t, J=2.0Hz, 2H); 8.29(d, J=4.7Hz, 2H) |
| 2 | C—CH=CH—CH=CH— | | C—CH=CH—CH=CH— | | Oil | 2941, 1585, 1547, 1511, 1484, 1402, 1359, 1307, 1260, 983, 750, 723 (film) | CDCl$_3$ | 1.6(m, 2H); 1.86(m, 2H); 2.27–2.45(a.c. 6H); 3.73 (t, J=5.2Hz, 4H); 4.30 (t, J=7.1Hz, 2H); 6.43 (t, J=4.7Hz, 2H); 7.12–7.46 (a.c. 6H); 8.07(d, J=6.5Hz, 2H) 8.26(d, J=4.7Hz, 2H) |
| 3 | C—CH=CH—CH=CH—C | | CH | H | Oil | 2940, 1585, | CDCl$_3$ | 1.54(m, 2H); 1.88(m, 2H); 2.37 (a.c. 6H); 2.79(t, J=5Hz, 4H); 4.13(t, J=6.8Hz, 2H); 6.45 (a.c. 2H); 6.9–7.1(a.c. 5H); 8.27(d, J=4.7Hz, 2H) |
| 4 | C—CH=CH—CH=CH—C | | CPh | Ph | Oil | 1586, 1547, 1502, 1447, 1359, 1261, 984, 789, 757, 702(film) | CDCl$_3$ | 1.38(m, 2H); 1.68(m, 2H); 2.10–2.40(a.c. 6H); 3.76 (t, J=5Hz, 2H); 6.41 (t, J=7Hz, 2H); 6.41 (t, J=4.7Hz, 2H); 7.10–7.50 (a.c. 13H); 7.79(m, 1H); 8.25(d, J=4.7 Hz, 2H) |
| 5 | N | CH | CH | O=CNH₂ | 124° C. | 3337, 3156, 1663, 1601, 1586, 1446, 1360, 980 (KBr) | DMSO-d$_6$ | 1.38(m, 2H); 1.81(m, 2H); 2.3–2.5(a.c. 6H); 3.69 (m, 4H); 4.14(t, J=7Hz, 2H); 6.6 (t, J=4, 7Hz, 1H); 7.0 (broad, 1H); 7.7 (broad, 1H); 7.89(s, 1H); (d, J=4.6Hz, 2H) |
| 6 | N | CH | CH | O=COH | 104–105° C. | 3100, 2943, 1587, 1602, 1546, 1487, 1440, 1360, 1260, 797 (film) | DMSO-d$_6$ | 1.40(m, 2H); 1.81(m, 2H); 2.23–2.49(a.c. 6H); 3.0 (broad, 1H); 3.64(m, 4H); 6.6 4.13(t, J=7Hz, 2H); 7.7(s, 1H); 8.1(s, 1H); 8.33(d, J=4.7Hz, 2H) |
| 7 | N | CMe | CCF₃ | H | 71–75° C. | 2937, 2856, 1586, 1544, 1496, 1393, 1228, 1177, 1125, 981 | CDCl$_3$ | 1.57(m, 2H); 1.89(m, 2H); 2.32 (s, 3H); 2.30–2.55(a.c. 6H); 3.82(t, J=5Hz, 4H); 4.10 (t, J=7Hz, 2H); 6.25(s, 1H); 6.47(t, J=4.7Hz, 1H); 8.29(d, J=4.7, 2H) |

TABLE I-continued

| | | | | | | IR | NMR solvent | NMR |
|---|---|---|---|---|---|---|---|---|
| 8 | CH | N | CPh | Ph | Oil | 2942, 1585, 1547, 1505, 1445, 1360, 1307, 1260, 983, 774, 754, 700 (KBr) | CDCl₃ | 1.55(m, 4H); 2.16-2.42 (a.c. 6H); 3.71-3.89 (a.c. 6H); 6.47(t, J=4.7Hz, 1H); 7.12-7.60(a.c. 11H); 8.27(d, J=4.7Hz, 2H) |
| 9 | CPh | N | CPh | Ph | Oil | 2942, 1585, 1546, 1501, 1445, 1360, 1260, 983, 698(film) | CDCl₃ | 1.55(m, 4H); 1.95-2.33 (a.c. 6H); 3.69-4.07(a.c. 6H); 6.47(t, J=4.7Hz, 1H); 7.13-7.67 (a.c. 15, H); 8.26(d, J=4.7Hz, 2H) |
| 10 | CMe | N | CPh | Ph | Oil | 2942, 1585, 1547, 1500, 1446, 1393, 1260, 983, 760, 698 (film) | CDCl₃ | 1.43(m, 4H); 2.18-2.47 (a.c. 9H); 3.72-3.76(a.c. 6H); 6.47(t, J=4.7Hz, 1H); 7.09-7.39 (a.c. 10H); 8.26(d, J=4.7Hz, 2H) |
| 11 | CMe | N | CCl | Cl | Oil | 2942, 1586, 1547, 1500, 1447, 1359, 1259, 1245, 983(film) | CDCl₃ | 1.45-1.84(a.c. 4H); 2.26-2.7 (a.c. 9H); 3.74-4.05(a.c. 6H); 6.48(t, J=4.7Hz, 1H); 8.30(d, J=4.7Hz, 2H) |
| 12 | CEt | N | CH | H | Oil | 2938, 1585, 1547, 1495, 1446, 1360, 1260, 983, 638(film) | CDCl₃ | 1.34(t, J=7, 1.3Hz); 1.66(m, 4H); 2.31-2.72(a.c. 8H); 3.77-3.92 (a.c. 6H); 6.47(t, J=4.7Hz, 1H); 6.87(d, J=10Hz, 2H); 8.26(d, J=4.7Hz, 2H) |
| 13 | CPh | N | CH | H | Oil | 2941, 1585, 1547, 1500, 1446, 1360, 1260, 983, 774, 700 (film) | CDCl₃ | 1.45(m, 2H); 1.73(m, 2H); 2.19-2.42(a.c. 6H); 3.77 (t, J=5.1Hz, 4H); 4.01 (t, J=7.3Hz, 2H); 6.47 (t, J=4.7Hz, 1H); 6.94-7.61 (a.c. 7H); 8.27(d, J=4.7Hz, 2H) |
| 14 | CH | N | CH | O=COMe | 92-94° C. | 2800, 1713, 1585, 1544, 1483, 1360, 1223, 1117, 985(KBr) | CDCl₃ | 1.45(m, 2H); 1.72(m, 2H); 2.29-2.39(a.c. 6H); 3.65-3.74 (a.c. 7H); 4.01(t, J=6.8Hz, 2H); 6.47(t, J=4.7Hz, 1H); 7.67 (s, 1H); 7.81(s, 1H); 8.24 (d, J=4.7Hz, 2H) |
| 15 | CH | N | CH | Ph | 105-107° C. | 2944, 1585, 1548, 1500, 1447, 1360, 1260, 983 (KBr) | DMSO-d₆ | 1.45(m, 2H); 1.73(m, 2H); 2.21-2.45(a.c. 6H); 3.60-3.75 (a.c. 4H); 4.03(t, J=6.8Hz, 2H); 6.47(t, J=4.7Hz, 1H); 7.21-7.79 (a.c. 7H); 8.25(d, J=4.7Hz, 2H) |
| 16 | CH | N | C—CH=CH—CH=CH— | | 85-88° C. | 2944, 1581, 1542, 1488, 1466, 1355, 1259, 741 (KBr) | DMSO-d₆ | 1.40(m, 2H); 1.82(m, 2H); 2.26-2.42(a.c. 6H); 3.62-3.71 (a.c. 4H); 4.24(t, J=6.9Hz, 2H); 6.56(t, J=4.7Hz, 1H); 7.16-7.26, (a.c. 2H); 7.55-7.70(a.c. 2H); |

TABLE 1-continued

| Example | $Z_1$ | $Z_4$ | $R_3$ | $Z_2$ | $Z_3$ | M.P. | IR cm$^{-1}$ | NMR solvent | $^1$H-NMR (100 MHz), δ, J=Hz |
|---|---|---|---|---|---|---|---|---|---|
| 17 | CH | N | | | C—N=CH—CH=CH— | 104° C. | 2935, 1578, 1545, 1482, 1443, 1409, 1357, 1256, 982, 751 (KBr) | DMSO-d$_6$ | 8.22-8.34(a.c. 3H) 1.45(m, 2H); 1.90(m, 2H); 2.23-2.50(a.c. 6H); 3.6 (t, J=4.8Hz, 4H); 4.3 (t, J=7.0Hz, 2H); 6.5 (t, J=4.7Hz, 2H); 7.25 (d, d, J=4.7Hz, 1H); 8.05 (d, J=7.9Hz, 1H); 8.30-8.48(a.c. 4H) |
| 18 | CH | N | | | C—CH=CH—CH=N— | 134° C. | 2344, 2828, 1609, 1582, 1543, 1487, 1460, 1355, 1260, 982, 800(KBr) | DMSO-d$_6$ | 1.42(m, 2H); 1.84(m, 2H); 2.28-2.49(a.c. 6H); 3.60-3.69 (a.c. 4H); 4.03(t, J=7.0Hz, 2H) 6.5(t, J=4.7Hz, 1H); 7.28 (dd, J=4.7Hz, 1H); 8.07 (d, J=7.9Hz, 1H); 8.29-8.50(a.c. 4H) |
| 19 | N | N | | | C—CH=CH—CH=CH— | 89-90.5° C. | 2940, 2818, 1590, 1544, 1498, 1360, 1259, 984, 749(KBr) | DMSO-d$_6$ | 1.43(m, 2H); 1.97(m, 2H); 2.24-2.53(a.c. 6H); 3.66 (t, J=5.1Hz, 4H); 4.75 (t, J=6.8Hz, 2H); 6.60 (t, J=4.7Hz, 1H); 7.52(m, 2H); 8.31(s, 1H); 8.36(s, 1H) |
| 20 | CCl | N | | | C—CH=CH—CH=CH— | 153-145° C. | 2940, 1583, 1542, 1491, 1466, 1443, 1383, 1264, 1128, 981, 742(KBr) | DMSO-d$_6$ | 1.50(m, 2H); 1.81(m, 2H); 2.20-2.42(a.c. 6H); 3.67 (m, 4H); 4.28(t, J=7Hz, 2H); 6.58(t, J=4.7Hz, 1H); 7.30 (m, 2H); 7.60(m, 2H); 8.31 (d, J=4.7Hz, 2H) |
| 21 | CH | C—CH=CH—C=CH— | Cl N | 82-84° C. | | 2945, 1583, 1544, 1492, 1356, 1260, 983, 799 (KBr) | CDCl$_3$ | 1.55(m, 2H); 1.34(m, 2H); 2.30-2.48(a.c. 6H); 3.75-3.85 (a.c. 4H); 4.16(t, J=7Hz, 2H) 6.45(t, J=4.7Hz, 1H); 7.27 (s, 1H); 7.34(dd, J=9Hz, J'=2Hz, 1H); 7.70(d, J=9Hz); 7.37 (d, J=2Hz, 1H); 8.27 (d, J=4.7Hz, 2H) |

TABLE I-continued

| 22 | CH | C—CH=C(Cl)—CH=CH—N | 91-93° C. | 2945, 1585, 1543, 1490, 1350, 1260, 983, 799 (KBr) | CDCl₃ | 1.55(m, 2H); 1.94(m, 2H); 2.30-2.48(a.c. 6H); 3.75-3.85, (a.c. 4H); 4.16(t, J=7Hz, 2H); 6.45(t, J=4.7Hz, 1H); 7.16 (dd, J=9Hz, J'=2Hz, 1H); 7.27 s, 1H); 7.83(d, J=9Hz, 1H); 7.87(d, J=2Hz, 1H); 8.27 (d, J=4.7Hz, 2H) |

| Example | Z₁ | Z₂ | R₃ | Z₄ | M.P. | IR cm⁻¹ | NMR solvent | ¹H-NMR (100 MHz), δ, J=Hz |
|---|---|---|---|---|---|---|---|---|
| 23 | CH | N | H | N | 69-71° C. | 2942, 1582, 1546, 1458, 1448, 1360, 1261, 1138, 1011, 983, 680,(KBr) | CDCl₃ | 1.55(m, 2H); 1.96(m, 2H); 2.32-2.51(a.c. 6H); 3.31 (t, J=5.1Hz, 4H); 4.21 (t, J=7.0Hz, 2H); 6.47 (t, J=4.7Hz, 2H); 7.95 (s, 1H); 8.09(s, 1H); 8.29(d, J=4.7Hz, 2H) |
| 24 | N | N | —CH=CH—CH=CH— | | 97.4-98.2° C. | 2946, 2863, 2823, 1585, 1547, 1483, 1358, 1256, 982, 799, 761(KBr) | DMSO-d₆ | 1.34-1.56(m, 2H); 1.97-2.13 (m, 2H); 2.18-2.48(a.c. 6H); 3.65(t, J=5.3Hz, 4H); 4.75 (t, J=6.8Hz, 2H); 6.56 (t, J=4.7Hz, 1H); 7.40 (dd, J=6.5Hz, J'=3.1Hz, 2H); 7.90(dd, J=6.6Hz, J'=3.3Hz, 2H); 8.28(s, 1H); 8.33(s, 1H) |
| 25 | CMe | C—CH=CH—CH=CH— | | | 101-102° C. | 2938, 2820, 1583, 1542, 1494, 1405, 1357, 1258, 983, 798, 744(KBr) | CDCl₃ | 1.56-1.93(a.c. 4H); 2.30-2.47 (a.c. 6H); 2.58(s, 3H); 3.79 (t, J=5.2Hz, 4H); 4.10 (t, J=7.3Hz, 2H); 6.43 (t, J=4.7Hz, 2H); 7.22(m, 3H); 7.67(m, 1H); 8.26(d, J=4.7Hz, 2H) |
| 26 | CH | C—CH=C—C=CH—<br>CH₃ CH₃ | | N | 105-106° C. | 2946, 1584, 1542, 1491, 1466, 1362, 1262, 983, 800, 742 (KBr) | CDCl₃ | 1.50(m, 2H); 1.85(m, 2H); 2.25-2.43(a.c. 12H); 3.76 (t, J=5.0Hz, 4H); 4.07 (t, J=7.0Hz, 2H); 6.40 (t, J=4.7Hz, 2H); 7.11(s, 1H); 7.51(s, 1H); 7.71(s, 1H); 8.23 (d, J=4.7Hz, 2H) |
| 27 | N | CH | H | CH | Oil | 2942, 2815, 1586, 1547, 983(film) | CDCl₃ | 1.50(m, 2H); 1.90(m, 2H); 2.40 (m, 6H); 3.80(m, 4H); 4.12 (t, 2H, J=6.9); 6.20(d, 1H), J=1.6); 6.40(t, 1H, J=4.7); 7.42(dd, 2H, J=4.7; J'=1.5); 8.25(d, 2H, J=4.7) |
| 28 | N | CMe | H | CMe | Oil | 1590, 1550, 1350, 1260, 980(film) | CDCl₃ | 1.58(m, 2H); 1.85(m, 2H); 2.20 (s, 3H); 2.25(s, 3H); 2.44 (m, 6H); 3.81(m, 4H); 3.97 (t, 2H, J=7.2); 5.78(s, 1H); 6.43(t, 1H, J=4.7); 8.27(d, 2H, J=4.7) |
| 29 | N | CMe | NO₂ | CMe | Oil | 1590, 1550, 1350, 1260, 980(film) | CDCl₃ | 1.60(m, 2H); 1.90(m, 2H); 2.49 (m, 9H); 2.63(s, 3H); 3.82 (m, 4H); 4.09(t, 2H, J=7); 6.48 (t, 1H, J=4.7); 8.29(d, 2H, J=4.7) |
| 30 | N | CH | Me | CH | Oil | 1590, 1550, 1500, 1360, 1260, 980 (film) | CDCl₃ | 1.52(m, 2H); 1.95(m, 2H); 2.05 (s, 3H); 2.37(m, 6H); 3.81 (m, 4H); 4.05(t, 2H, J=6.8); 6.41(t, 1, H, J=4.7); 7.13 (s, 1H); 7.27(s, 1H); 8.23(d, 2H, J=4.7) |
| 31 | N | CH | —CH=CH—CH=CH— | | Oil | 2930, 1590, 1550, 1500, 1360, 1310, 1260, 980 (film) | CDCl₃ | 1.51(m, 2H); 1.98(m, 2H); 2.36 (m, 6H); 3.77(m, 4H); 4.39 (t, 2, H, J=6.9); 6.40(t, 1H, J=4.7); 7.0-7.7(m, 4H); 7.95 (s, 1H); 8.25(d, 2H, J=4.7) |

| # | | | | | | | |
|---|---|---|---|---|---|---|---|
| 32 | N | CMe | Br' | CMe | Oil | 2930, 1590, 1550, 1500, 1360, 1310, 1260, 980 (film) | CDCl₃ | 1.55(m, 2H); 1.81(m, 2H); 2.18 (s, 3H); 2.20(s, 3H); 2.38 (m, 4H); 3.80(m, 4H); 3.99 (t, 2H, J=6.9); 6.42(t, 1H, J=4.7); 8.25(d, 2H, J=4.7) |
| 33 | N | CH | NO₂ | CH | 94–96° C. | 1584, 1524, 1480, 1444, 1406, 1359, 1305, 819 (KBr) | CDCl₃ | 1.5(m, 2H); 1.93(m, 2H); 2.38 (m, 6H); 3.76(m, 4H); 4.15 (t, 2H, J=6.7); 6.42(t, 1H, J=4.7); 8.01(s, 1H); 8.12 (s, 1H); 8.24(d, 2H, J=4.7) |
| 34 | N | CH | Cl | CH | Oil | 2843, 1586, 1547, 1358, 983(film) | CDCl₃ | 1.52(m, 2H); 1.90(m, 2H); 2.43 (m, 6H); 3.80(m, 4H); 4.0 (t, 2H, J=6.8); 6.44(t, 1H, J=4.7); 7.35(s, 1H); 7.39 (s, 1H); 8.25(d, 2H, J=4.7) |
| 35 | N | CH | EtOOC— | CH | Oil | 1715, 1586, 1222, 983. (film) | CDCl₃ | 1.34(t, 3H, J=7.1); 1.54(m, 2H); 1.90(m, 2H); 2.46(m, 6H); 3.81 (m, 4H); 4.25(m, 4H); 6.47 (t, 1H, J=4.7); 7.90(s, 2H); 8.29(d, 2H, J=4.7) |
| 36 | N | CMe | H | CPh | Oil | 1586, 1547, 1360, 983 (film) | CDCl₃ | 1.54(m, 2H); 1.85(m, 2H); 2.28 (s, 3H); 2.45(m, 6H); 3.81 (m, 4H); 4.07(t, 2H, J=7); 6.28 (s, 1H); 6.43(t, 1H, J=4.7); 7.33(m, 4H); 7.75(m, 2H); 8.26(d, 2H, J=4.7) |
| 37 | N | CH | Br | CH | Oil | 1586, 1547, 1360, 984 (film) | CDCl₃ | 1.52(m, 2H); 1.89(m, 2H); 2.44 (m, 6H); 3.62(m, 4H); 4.11 (t, 2H, J=6.7); 6.46(t, 1H, J=4.6); 7.42(t, 1H); 7.45 (s, 1H); 8.29(d, 2H, J=4.6) |
| 38 | N | CH | C≡N | CH | 94–95° C. | 3076, 2231, 1587, 1551, 1258, 982 (KBr) | CDCl₃ | 1.54(m, 2H); 1.96(m, 2H); 2.40 (m, 6H); 3.81(m, 4H); 4.20 (t, 2H, J=6.9); 6.48(t, 1H, J=4.7); 7.80(s, 1H); 7.83 (s, 1H); 8.29(d, 2H, J=4.7) |
| 39 | N | CH | F | CH | Oil | 2944, 1584, 1546, 1507, 1359, 1260, 983 (film) | CDCl₃ | 1.45(m, 2H); 1.96(m, 2H); 2.36 (m, 6H); 3.77(m, 4H); 4.0 (t, 2H, J=6.9); 6.47(t, 1H, J=4.7); 7.27(m, 2H, J=4.8); 8.29(d, 2H, J=4.8) |
| 40 | N | CH | Me—O— | CH | Oil | 2940, 1585, 1547, 1470, 1359, 1122, 983 (film) | CDCl₃ | 1.54(m, 2H); 1.89(m, 2H); 2.42 (m, 6H); 3.77(m, 7H); 4.06 (m, 2H); 6.42(t, 1H, J=4.7); 7.02(s, 1H); 7.26(m, 2H); 8.25(d, 2H, J=4.6) |
| 41 | CH | N | H₂N— | N | Oil | 1586, 1548, 1360, 984 (film) | CDCl₃ | 1.50(m, 2H); 1.85(m, 2H); 2.43(m, 6H); 3.4(broad 2H); 3.8(m, 6H); 4.0 (t, 2H, J=6.4); 6.46(t, 1H, J=4.7); 6.98(s, 1H); 7.10 (s, 1H); 8.27(d, 2H, J=4.7) |
| 42 | CH | CH | Me—SO₂—NH— | N | 132° C. | 1582, 1482, 1360, 1150, 983 (KBr) | CDCl₃ | 1.58(m, 2H); 1.93(m, 2H); 2.45(m, 6H); 2.94(s, 3H); 3.8(m, 4H); 4.11(t, 2H, J=6.9); 6.45(t, 1H, J=4.7) |

| | | | | | | | |
|---|---|---|---|---|---|---|---|
| 43 | CH | CH | Ph—CO—NH— | N | 134-136° C. | 1646, 1586, 1542, 1369, (KBr) | CDCl₃ | 7.4(s, 1H); 7.5(s, 1H); 8.28(d, 2H, J=4.7) 1.55(m, 2H); 1.79(s, 3H); 1.88(m, 2H); 2.42(m, 6H); 3.80(m, 4H); 4.13(t, 2H, J=6.8); 6.51(t, 1H, J=4.7) 7.49(m, 4H); 7.83(m, 2H); 8.0(s, 1H); 8.11(s, 1H); 8.28(d, 2H, J=4.7) |
| 44 | CH | CH | Me—CO—NH— | N | 80-82° C. | 1650, 1586, 1454, 1364, 1261, 98.3 (KBr) | CDCl₃ | 1.50(m, 2H); 1.88(m, 2H); 2.11(s, 3H); 2.43(m, 6H); 3.79(m, 4H); 4.8(t, 2H, J=6.8); 6.47(t, 1H, J=4.7) 7.36(s, 1H); 7.93(s, 1H); 8.28(d, 2H, J=4.6); 9.25 (s, 1H) |
| 45 | CH | CH | Me<br>\|<br>CH—NH—<br>\|<br>Et | N | Oil | 2960, 1585, | CDCl₃ | 1.00(t, 3H, J=7.0); 1.19 (d, 3H, J=6.3); 1.6(m, 4H); 1.90(m, 2H); 2.50(m, 6H); 3.0(m, 3H); 3.9(m, 4H); 4.1(t, 2H, J=6.8); 6.52 (t, 1H, J=4.7); 6.99(s, 1H) 7.17(s, 1H); 3.37(d, 2H, J=4.7) |
| 46 | N | CH | H | OMe | Oil | 1547, 1359, 1260, 983 (film) | | 1.50(m, 2H); 1.80(m, 2H); 2.29(s, 3H); 2.39(m, 6H); 3.82(m, 4H); 4.04(m, 2H, J=6.9); 5.97(s, 1H); 6.40 (t, 1H, J=4.7); 7.34(d, 1H, J=2.1); 8.24(d, 2H, J=4.7) |
| 47 | N | OMe | H | CH | Oil | 1585, 1550, 1500, 1450, 1360, 980 (film) | CDCl₃ | 1.52(m, 2H); 1.81(m, 2H); 2.25(s, 3H); 2.44(m, 6H); 3.81(m, 4H); 4.03(m, 2H); 5.95(s, 1H); 6.42(t, 1H, J=4.7); 7.23(d, 1H, J=2.1); 8.27(d, 2H, J=4.7) |
| 48 | N | CH | Br | OMe | Oil | 1590, 1550, 1500, 1450, 1360, 1260, 980 (film) | CDCl₃ | 1.52(m, 2H); 1.83(m, 2H); 2.26(s, 3H); 2.45(m, 6H); 3.80(m, 4H); 6.45(t, 1H, J=4.7); 7.38(d, 1H, J=1.8) 8.27(d, 2H, J=4.7) |
| 49 | N | OMe | Br | CH | Oil | 1590, 1550, 1500, 1450, 1360, 1260, 980 (film) | CDCl₃ | 1.53(m, 2H); 1.84(m, 2H); 2.22(s, 3H); 2.45(m, 6H); 3.80(m, 4H); 6.46(t, 1H, J=4.7); 7.31(d, 1H, J=1.7); 8.29(d, 2H, J=4.7) |

| No. | | | | mp | IR | Solvent | NMR |
|---|---|---|---|---|---|---|---|
| 50 | N | CH | —C—(CH₂)₄— | Oil | 2930, 1590, 1550, 1450, 1360, 1310, 1260, 980 (film) | CDCl₃ | 1.70(m, 8H); 2.45(m, 10H); 3.8(m, 4H); 3.97(t, 2H, J=6.9); 6.45(t, 1H, J=4.7); 7.05(d, 1H, J=1.8); 8.27 (d, 2H, J=4.7) |
| 51 | N | CH | —(CH₂)₄—C— CH | Oil | 2930, 1590, 1500, 1450, 1360, 1310, 1260, 980 (film) | | 1.70(m, 8H); 2.45(m, 10H); |
| 52 | N | OMe | Ph | Oil | 1590, 1550, 1500, 1450, 1360, 1310, 1260, 980 (film) | CDCl₃ | 1.50(m, 2H); 1.90(m, 2H); 2.39(s, 3H); 2.50(m, 6H); 3.80(m, 4H); 4.1(t, 2H, J=6.9); 6.44(t, 1H, J=4.7); 7.35(m, 6H); 8.27(d, 2H, J=4.7) |
| 53 | N | OMe | Ph | Oil | 1590, 1550, 1500, 1450, 1360, 1310, 1260, 980 (film) | CDCl₃ | 1.50(m, 2H); 1.90(m, 2H); 2.40(s, 3H); 2.51(m, 6H); 3.81(m, 4H); 4.09(t, 1H, J=6.9); 6.44(t, 1H, J=4.7); 7.34(m, 6H); 8.28(d, 2H, J=4.7) |
| 54 | N | CCl | F | Oil | 2944, 1585, 1547, 1507, 1360, 1260, 984 (film) | CDCl₃ | 1.52(m, 2H); 1.90(m, 2H); 2.40(m, 6H); 3.80(m, 4H); 4.0(t, 2H, J=4.8); 6.45 (t, 1H, J=4.7); 7.30(d, 1H, J=4.8); 8.29(d, 2H, J=4.8) |
| 55 | N | CCl | Me—O | Oil | 2940, 1586, 1470, 1360, 1121, 983 (film) | CDCl₃ | 1.53(m, 2H); 1.90(m, 2H); 2.4(m, 6H); 3.8(m, 7H); 4.0(m, 2H); 6.4(t, 1H, J=4.8); 7.0(s, 1H); 7.25 (s, 1H); 8.2(d, 2H, J=4.8); 1.62(m, 2H); 1.88(m, 2H); |
| 56 | N | CH | CH, 4-MeO-phenyl | 79–82° C. | 2390, 1589, 1545, 1495, 1360, 1247, 983, 833, 799 (KBr) | | 2.45(m, 6H); 3.81(m, 7H); 4.16(t, 2H, J=6.8); 6.46 (t, 1H, 3–4.7); 6.9(d, 2H, J=4.4); 7.4(d, 2H, J=4.4); 7.55(s, 1H); 7.7(s, 1H) 8.28(d, 2H, J=2.4) 1.6(m, 2H); 1.9(m, 2H); |
| 57 | N | CH | CH, 4-O-phenyl | 108–110° C. | 2946, 1586, 1549, 1485, 1395, 1257, 982, 951, 830 (KBr) | CDCl₃ | 2.46(m, 6H); 3.8(m, 4H); 4.16(t, 2H, J=6.8); 6.4 (t, 1H, J=4.7); 7.36(d, 4H, J=1.3); 7.7(d, 2H, J=6.2); 8.28(d, 2H, J=2.3) |

-continued

| | | | | | | |
|---|---|---|---|---|---|---|
| 58 | N | CH | (pyrrole) | CH | Oil | 2943, 1586, | | 1.55(m, 2H); 1.80(m, 2H) |
| 59 | N | CH | (phenyl) | CH | 1487, 1359, 1260, 984, 726 (film) | CDCl₃ | 2.45(m, 6H); 3.81(t, 4H, J=5); 4.12(t, 2H, J=7); 6.25(2H, t, J=2); 6.44(1H, t, J=4.7); 6.84(m, 2H); 7.5(d, 2H, J=5); 8.27(d, 2H, J=4.7); 1.6(m, 2H); 1.9(m, 2H) |
| 60 | N | CPh | H | CPh | 39–42° C. | 2942, 1585, 1493, 1446, 1359, 1485, 983, 760 (film) | CDCl₃ | 2.5(m, 4H); 3.8(m, 6H); 4.2(t, 2H, J=6.8); 6.7 (t, 1H, J=4.7); 7.2–7.7 (arms. compl. 5H); 8.0 (s, 1H); 8.2(s, 1H); 8.4 (d, 2H, J=2.3) 1.6(m, 2H); 1.9(m, 2H) |
| 61 | N | CH | –SO₂NH– (phenyl) | CH | 80–82° C. | 2942, 1585, 1547, 1485, 1359, 1260, 983, 763, 697 (film) | CDCl₃ | 2.35(m, 6H); 3.8(m, 4H); 4.2(t, 2H, J=6.8); 6.4 (t, 1H, J=4.7); 6.6(s, 1H); 7.2–7.4(abs. compl. 8H); 7.8(m, 2H); 8.25(d, 2H, J=2.4) 1.45(m, 2H); 1.85(m, 2H) |
| 62 | N | CH | Me-phenyl-SO₂NH– | CH | 92–95° C. | 2931, 1584, | CDCl₃ | 2.40(m, 6H); 3.80(m, 4H); 4.0(t, 2H, J=6.7); 6.47 (t, 1H, J=4.6); 7.0(s, 1H); 7.5(m, 6H); 8.3(d, 2H, 2 J=4.6) 1.5(m, 2H); 1.85(m, 2H) |
| | | | | | 108–110° C. | 1548, 1490, 1167, 1358, 983 (KBr) | | |
| 63 | N | CH | n-Bu-SO₂-NH– | CH | Oil | 1548, 1446, 1360, 1161, 984 (KBr) | | 2.28(m, 9H); 3.8(m, 4H); 4.0(m, 2H); 6.45(t, 1H, J=4.7); 7–7.65(m, 6H); 8.27(d, 2H, J=4.7) |
| | | | | | | 2941, 1448, 1548, 1360, 1146, 984, 755 (film) | CDCl₃ | 0.91(t, 3H, J=6.8); 1.45 (m, 4H); 1.85(m, 4H); 2.40 (m, 6H); 3.0(m, 2H); 3.80 (m, 4H); 4.11(t, 2H, J=6.5); 6.5(t, 1H, J=4.7); 7.4 |

| | | | | | | |
|---|---|---|---|---|---|---|
| 64 | N | CH | n-Pr—SO₂—NH— | CH | Oil | 2940, 1586, 1548, 1447, 1360, 1146, 984, 755 (film) | CDCl₃ | (m, 2H); 7.5(s, 1H); 8.3 (d, 2H, J=4.7) 1.0(t, 3H, J=7.1); 1.55 (m, 2H); 1.9(m, 4H); 2.45 (m, 6H); 3.0(t, 2H, J=7.4); 3.8(m, 4H); 4.1(t, 2H, J=6.4); 6.46(t, 1H, J=4.7); 7.35(m, 2H); 7.5(s, 1H); 8.3(d, 2H, J=4.7) |
| 65 | N | CH | Et—SO₂—NH— | CH | Oil | 2943, 1586, 1548, 1447, 1360, 1146, 984, 754 (film) | CDCl₃ | 1.36(m, 5H); 1.9(m, 2H); 2.45(m, 6H); 3.0(m, 2H); 3.6(m, 4H); 4.1(t, 2H, J=6.4); 6.45(t, 1H, J=4.7); 7.39(s, 1H); 7.51(s, 1H); 8.3(d, 2H, J=4.7). |
| 66 | N | OMe | —SO₂—N—Me₂ | OMe | Oil | 2939, 1586, 1547, 1448, 1360, 1290, 983, 951, 788 (film) | CDCl₃ | 1.7(m, 4H); 2.3–3.0(abs. compl. 18H); 3.8(m, 4H); 4.0(t, 2H, J=6.8); 6.5 (t, 1H, J=4.7); 8.2(d, 2H, J=2.35) |
| 67 | N | CH | —SO₂—N—Me₂ | CH | 100–102° C. | 3135, 2943, 1586, 1512, 1357, 1328, 1156, 982, 728 (KBr) | CDCl₃ | 1.6(m, 2H); 1.9(m, 2H); 2.3–2.7(abs. compl. 13H); 3.8(m, 4H); 4.2(t, 2H, J=6.8); 6.4(t, 1H, J=4.7); 7.75(d, 1H, J=4.4); 8.28 (d, 2H, J=2.4) |
| 68 | N | CH | —SO₃—H | CH | 230–235° C. | 3330, 1590, 1556, 1449, 1220, 1178, 1049, 971, 656 (KBr) | D₂O | 1.95(m, 2H); 3.3(m, 6H); 4.0(s, 5H); 4.27(t, 2H, J=6.1); 6.8(t, 1H, J=4.8); 7.8(s, 1H); 8.0(s, 1H); 8.43(d, 2H, J=2.4) |
| 69 | CH | N | H | CH | Oil | 2940, 1585, 1500, 1360, 1260, 975, (film) | CDCl₃ | 1.6(m, 2H); 1.8(m, 2H); 2.5(m, 6H); 3.80(m, 6H); 6.5(t, 1H, J=4.7); 6.9 (s, 1H); 7.1(s, 1H); 7.5 (s, 1H); 8.4(d, 2H, J=4.7) |
| 70 | OMe | N | H | CH | Oil | 2941, 1586, 1547, 1499, 1359, 1259, 983 (film) | CDCl₃ | 1.72(m, 4H); 2.37(s, 3H); 2.44(m, 6H); 3.80(m, 6H); 6.45(t, 1H, J=4.7); 6.85 (d, 2H, J=4.5); 8.27(d, 2H, J=4.7) |
| 71 | CH | N | Cl | CCl | 69–71° C. | 2946, 1584, 1543, 1492, 1359, 1254, 983, 797 (KBr) | CDCl₃ | 1.4–2.1(abs. compl. 4H); 2.46(m, 6H); 3.86(m, 6H); 6.47(t, 1H, J=4.7); 7.38 (s, 1H); 8.29(d, 2H, J=4.7) |
| 72 | CH | N | Me | CH | Oil | 2942, 1585, 1548, 1447, 1359, 1260, 984, 735 (film) | CDCl₃ | 1.4–2.0(abs. compl. 4H); 2.21(s, 3H); 2.45(m, 6H); 3.82(m, 6H); 6.47(t, 1H, J=4.7); 6.62(s, 1H); 7.35 (s, 1H); 8.28(d, 2H, J=4.7) |
| 73 | CH | N | H | OMe | Oil | 2942, 1585, 1548, 1446, 1359, 1260, 984, 736 (film) | CDCl₃ | 1.4–2.0(abs. compl. 4H); 2.20(s, 3H); 2.45(m, 6H); 3.82(m, 6H); 6.47(t, 1H, J=4.7); 6.79(s, 1H); 7.40 (s, 1H); 8.28(d, 2H, J=4.7) |

TABLE II

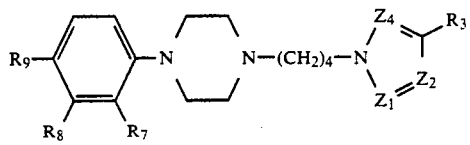

| Example | $Z_1$ | $Z_2$ | $R_3$ | $Z_4$ | $R_7$ | $R_8$ | $R_9$ | M.P. | IR cm$^{-1}$ | NMR solvent | $^1$H-NMR (100 MHz), δ, J=Hz |
|---|---|---|---|---|---|---|---|---|---|---|---|
| 74 | N | CH | Cl | CH | H | H | MeO— | 76–77° C. | 2833, 1511, 1448, 1247, 1029, 979, 824 (KBr) | DMSO-d$_6$ | 1.43 (m, 2H); 1.78 (m, 2H); 1.71–2.48 (a.c. 6H); 2.93–3.02 (m, 4H); 3.67 (s, 3H); 4.09 t, J=6.8Hz, 2H); 6.83 (s, 4H); 7.52 (s, 1H); 7.98 (s, 1H) |
| 75 | CMe | N | Cl | CCl | H | H | MeO— | 73–75° C. | 2940, 2818, 1512, 1457, 1245, 1183, 1036, 826 (KBr) | DMSO-d$_6$ | 1.33–1.87 (a.c. 4H); 2.32 (s, 3H); 2.41–2.51 (a.c. 6H); 2.82–3.0 (m, 4H); 3.67 (s, 3H); 3.93 (t, J=7.2Hz, 2H); 6.83 (s, 4H) |
| 76 | N | CH | Cl | CH | MeO— | H | H | Oil | 2941, 2816, 1500, 1450, 1241, 749, (film) | DMSO-d$_6$ | 1.39 (m, 2H); 1.77 (m, 2H); 2.22–2.45 (a.c. 6H); 2.92 (m, 4H); 3.76 (s, 3H); 4.07 (t, J=6.0Hz, 2H); 6.87 (m, 4H); 7.51 (s, 1H); 7.95 (s, 1H) |
| 77 | CMe | N | Cl | CCl | MeO— | H | H | 82–83° C. | 2943, 2820, 1502, 1405, 1241, 1030, 746 (KBr) | DMSO-d$_6$ | 1.43–1.60 (a.c. 4H); 2.33 (s, 3H); 2.40–2.50 (a.c. 6H); 2.95 (m, 4H); 3.76 (s, 3H); 3.93 (t, J=7.0Hz, 2H); 6.89 (m, 4H) |
| 78 | N | CH | Cl | CH | H | MeO— | H | Oil | 2943, 2820, 1601, 1578, 1496, 1451, 1203, 1171, 970 (film) | CDCl$_3$ | 1.52 (m, 2H); 1.85 (m, 2H); 2.28–2.56 (a.c. 6H); 3.16 (m, 4H); 3.7 (s, 3H); 4.05 (t, J=7.0Hz, 2H); 6.4 (m, 3H); 7.15 (m, 1H); 7.34 (s, 1H); 7.40 (s, 1H) |
| 79 | CH | CH | H | CH | H | H | MeO— | Oil | 2943, 2815, 1512, 1455, 1244, 1037, 823, 724 (film) | CDCl$_3$ | 1.50–1.80 (a.c. 4H); 2.31–2.61 (a.c. 6H); 3.06 (m, 4H); 3.74 (s, 3H); 3.81 (t, J=7.0Hz, 2H); 6.1 (m, 2H); 6.6 (m, 2H); 6.84 (s, 4H) |
| 80 | CH | CH | | | MeO— | H | H | Oil | 2940, 2814, 1500, 1451, 1281, 1241, 1028, 743, 723 (film) | CDCl$_3$ | 1.50–1.85 (a.c. 4H); 2.33–2.66 (a.c. 6H); 3.10 (m, 4H); 3.84–3.96 (a.c. 5H); 6.12 (t, J=2Hz, 2H); 6.65 (t, J=2Hz, 2H); 6.93 (m, 4H) |
| 81 | CH | CH | H | CH | H | H | H | Oil | 2943, 2817, 1600, 1501, 1235, 759, 723, 692 (film) | CDCl$_3$ | 1.41–1.89 (a.c. 4H); 2.37 (t, J=7.3Hz, 2H); 2.50–2.60 (a.c. 4H); 3.18 (m, 4H); 3.89 (t, J=6.9Hz, 2H); 6.13 (t, J=2.0Hz, 2H); 6.64 (t, J=2.0Hz, 2H); 6.83–7.33 (a.c. 5H) |
| 82 | N | CH | Cl | CH | H | H | H | 58–61° C. | 2942, 2819, 1600, 1500, 1450, 1381, 1311, 1240, 1140, 966, 756 (KBr) | CDCl$_3$ | 1.47 (m, 2H); 1.84 (m, 2H); 2.35 (t, J=7.2Hz, 2H); 2.52 (m, 4H); 3.16 (m, 4H); 4.04 (t, J=6.8Hz, 2H); 6.75–6.94 (a.c. 3H); 7.16 (s, 1H); 7.23 (s, 1H); 7.35 (d, J=7.4Hz, 2H) |
| 83 | CMe | N | Cl | CCl | H | H | H | Oil | 2944, 2819, 1600, 1532, 1503, 1453, 1404, 1244, 1143, 759, 692 (film) | CDCl$_3$ | 1.43–1.87 (a.c. 4H); 2.33 (s, 3H); 2.38–2.60 (a.c. 6H); 3.17 (m, 4H); 3.83 (t, J=7Hz, 2H); 6.9 (a.c. 3H); 7.24 (m, 2H) |
| 84 | N | CH | Cl | CH | Cl | H | H | Oil | 2943, 2817, 1587, 1480, 1443, 1231, 1040, 971, 751, 612 (film) | DMSO-d$_6$ | 1.40 (m, 2H); 1.78 (m, 2H); 2.2–2.6 (a.c. 6H); 2.95 (m, 4H); 4.08 (t, J=6.5Hz, 2H); 6.95–7.41 (a.c. 4H); 7.50 (s, 1H); 7.97 (s, 1H) |
| 85 | CMe | N | Cl | CCl | Cl | H | H | 89–91° C. | 2936, 2818, 1587, 1531, 1480, 1359, 1243, 1229, 1036, 1016 (KBr) | CDCl$_3$ | 1.3–1.8 (a.c. 4H); 2.33 (s, 3H); 2.35–2.70 (a.c. 6H); 2.96 (m, 4H); 3.94 (t, J=7.2Hz, 2H); 6.90–7.50 (a.c. 4H) |
| 86 | N | CH | Cl | CH | H | Cl | H | Oil | 2944, 2820, 1594, 1564, 1487, 1451, 1433, 1384, 1239, 987, | CDCl$_3$ | 1.3–1.70 (m, 2H); 1.70–2.10 (m, 2H); 2.39 (T, J=7.4Hz, 2H); 2.59 (m, 4H); 3.17 (m, 4H); 4.09 (t, J=7.4Hz, 2H); 6.7–6.9 (a.c. 3H); 7.15 (t, J=8.0Hz, 1H) |

TABLE II-continued

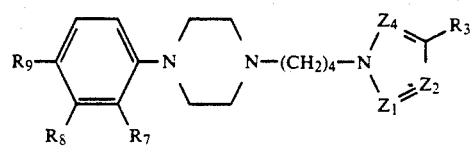

| Example | $Z_1$ | $Z_2$ | $R_3$ | $Z_4$ | $R_7$ | $R_8$ | $R_9$ | M.P. | IR cm$^{-1}$ | NMR solvent | $^1$H-NMR (100 MHz), δ, J=Hz |
|---|---|---|---|---|---|---|---|---|---|---|---|
| | | | | | | | | | 980 (film) | | 7.37 (s, 1H); 7.4 (s, 1H) |

TABLE III

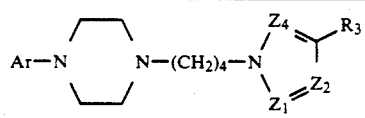

| Example | $Z_1$ | $Z_2$ | $Z_4$ | $R_3$ | Ar | M.P. | IR cm$^{-1}$ | NMR solvent | $^1$H-NMR (100 MHz), δ, J=Hz |
|---|---|---|---|---|---|---|---|---|---|
| 87 | N | CH | CH | H | (N-methylimidazolyl) | Oil | 2943, 2812, 1525, 1509, 1469, 1455, 1282, 1137, 751 (film) | CDCl$_3$ | 1.52 (m, 2H); 1.91 (m, 2H); 2.30–2.60 (a.c. 6H); 3.08 (m, 4H); 4.15 (t, J=7Hz, 2H); 6.22 (t, J=2Hz, 1H); 6.64 (d, J=1.4Hz, 1H); 6.76 (d, J=1.4Hz, 1H); 7.38 (d, J=2Hz, 1H); 7.48 (d, J=2Hz, 1H) |
| 88 | N | CH | CH | Cl | benzisothiazolyl | Oil | 2943, 2815, 1493, 1451, 1423, 1383, 1307, 1261, 970, 739, 613 (film) | CDCl$_3$ | 1.50 (m, 2H); 1.85 (m, 2H); 2.45 (t, J=7.2Hz, 2H); 2.60 (t, J=4.7Hz, 4H); 3.53 (t, J=5.0Hz, 4H); 4.07 (t, J=7.0Hz, 2H); 7.35 (m, 4H); 7.85 (m, 2H) |
| 89 | CMe | N | CCl | Cl | benzisothiazolyl | Oil | 2944, 2816, 1533, 1493, 1422, 1380, 1280, 1246, 1139, 1017, 754, 665 (film) | CDCl$_3$ | 1.55–1.85 (a.c. 4H); 2.34–2.49 (a.c. 5H); 2.62 (t, J=4.7Hz, 4H) 3.53 (t, J=5.0Hz, 4H); 3.84 (t, J=7.0Hz, 2H); 7.37 (m, 2H); 7.83 (m, 2H) |
| 90 | N | CH | CH | Br | 5-bromopyrimidinyl | 84.6° C. | 2952, 1583, 1526, 1365, 1311, 950 (KBr) | CDCl$_3$ | 1.57 (m, 2H); 1.90 (m, 2H); 2.45 (m, 6H); 3.80 (t, 4H, J=6.8); 7.44 (d, 2H, J=4); 8.29 (s, 2H) |
| 91 | N | CH | CH | Cl | 5-bromopyrimidinyl | 85–86° C. | 1585, 1525, 1495, 1364 (KBr) | CDCl$_3$ | 1.50 (m, 2H); 1.86 (m, 2H); 2.40 (m, 6H); 3.76 (m, 4H); 4.08 (m, 2H); 7.4 (t, 2H, J=6.9); 8.25 (s, 2H) |
| 92 | CMe | N | CH | H | pyrimidinyl | Oil | 2941, 1586, 1547, 1499, 1359, 1259, 983 (film) | CDCl$_3$ | 1.72 (m, 4H); 2.37 (s, 3H); 2.44 (m, 6H); 3.80 (m, 6H); 6.45 (t, 1H), J=4.7); 6.85 (d, 2H, J=4.5); 8.27 (d, 2H, J=4.7) |

What is claimed is:

1. A process for the preparation of an aryl (or heteroaryl) piperazinylbutylazole compound corresponding to the formula I

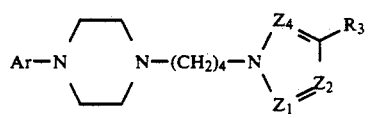

in which

Ar denotes a radical selected from the group consisting of phenyl, pyrimidinyl, imidazolyl and benzoisothiazole groups, unsubstituted or substituted with at least one substituent of the group consisting of methoxy, methyl and halo, $Z_1$ denotes a nitrogen atom or a C-$R_1$ group, $Z_2$ denotes a nitrogen atom or a C-$R_2$ group, $Z_4$ denotes a nitrogen atom or a C-$R_4$ group, and $R_1$, $R_2$, $R_3$ and $R_4$, which are identical or different are each selected from the group consisting of a hydrogen atom, a halogen, a lower alkyl radical, a nitro radical, a hydroxyl radical, an alkoxy radical, a cyano radical, a carboxylic radical, a carboxamido radical, an alkylcarboxylate radical, an aryl radical, a sulfonic radical, a sulfonamido radical and an amino radical, $Z_1$, $Z_2$, $Z_4$ and $R_3$ also including choices so that $Z_1$ and $Z_2$ together, $Z_2$ and $Z_3$ together and $Z_4$ and $R_3$ together may form one or two additional rings to provide, with the five-membered ring containing $Z_1$, $Z_2$ and $Z_4$, a multiring structure of the group consisting of pyrrole, carbazole, indole, benzimidazole, imidazopyridine, benzotriazole, indazole and tetrahydroindazole rings, wherein a compound of formula IX

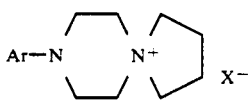 (IX)

in which

Ar has the meanings referred to above and X denotes a halogen atom, is reacted with a compound of formula III

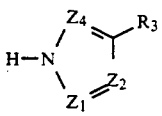 (III)

in which $Z_1$, $Z_2$, $Z_4$ and $R_3$ have the meanings referred to above.

2. The process for the preparation as claimed in claim 1, wherein the reaction takes place in the presence of at least one solvent selected from the group consisting of dimethyl sulfoxide, dimethylformamide, $C_2$ to $C_4$ alcohols, an aliphatic or aromatic hydrocarbon and an ether.

3. The process for the preparation as claimed in claim 2, wherein the solvent is dimethylformamide.

4. The process as claimed in claims 1, 2, or 3, wherein the reaction is conducted in the presence of an inorganic or organic base.

5. The process of claim 4 wherein said base is an inorganic base of the group consisting of alkali metal hydroxides, carbonates and bicarbonates.

6. The process as claimed in claim 5, wherein the base is potassium carbonate.

7. The process as claimed in one of claims 2 or 3, wherein the reaction is carried out at a temperature between room temperature and the boiling temperature of the solvent and with a reaction time of between 1 hour and 24 hours.

8. A process for the preparation of the compounds corresponding to the formula I as claimed in claim 1, which are selected from the following group:

1 - 1-{4-[4-(2-pyrimidinyl)-1-piperazinyl]butyl}pyrrole,
2 - 1-{4-[4-(2-pyrimidinyl)-1-piperazinyl]butyl}-carbazole,
3 - 1-{4-[4-(2-pyrimidinyl)-1-piperazinyl]butyl}indole,
4 - 2,3-diphenyl-1-{4-(4-[4-(2-pyrimidinyl)-1-piperazinyl]-butyl}indole,
5 - 4-carboxamido-1-{4-[4-(2-pyrimidinyl)-1-piperazinyl]butyl}-1H-pyrazole,
6 - 4-carboxy-1-{4-[4-(2-pyrimidinyl)-1-piperazinyl]-butyl}-1H-pyrazole,
7 - 3-methyl-5-trifluoromethyl-1-{4-[4-(2-pyrimidinyl)-1-piperazinyl]butyl}-1H-pyrazole,
8 - 4,5-diphenyl-1-{4-[4-(2-pyrimidinyl)-1-piperazinyl]-butyl}-1H-imidazole,
9 - 2,4,5-triphenyl-1-{4-[4-(2-pyrimidinyl)-1-piperazinyl]butyl}-1H-imidazole,
10 - 4,5-diphenyl-2-methyl-1-{4-[4-(2-pyrimidinyl)-1-piperazinyl]butyl}-1H-imidazole,
11 - 4,5-dichloro-2-methyl-1-{4-[4-(2-pyrimidinyl)-1-piperazinyl]butyl}-1H-imidazole,
12 - 2-ethyl-1-{4-[4-(2-pyrimidinyl)-1-piperazinyl]-butyl}-1H-imidazole,
13 - 2-phenyl-1-{4-[4-(2-pyrimidinyl)-1-piperazinyl]-butyl}-1H-imidazole,
14 - methyl 1-{4-[4-(2-pyrimidinyl)-1-piperazinyl]-butyl}-1H-imidazole-4-carboxylate,
15 - 4-phenyl-1-{4-[4-(2-pyrimidinyl)-1-piperazinyl]-butyl}-1H-imidazole,
16 - 1-{4-[4-(2-pyrimidinyl)-1-piperazinyl]butyl}-1H-benzimidazole,
17 - 1-{4-[4-(2-pyrimidinyl)-1-piperazinyl]butyl}-3H-imidazo[5,4-b]pyridine,
18 - 1-{4-[4-(2-pyrimidinyl)-1-piperazinyl]butyl}-1H-imidazo[4,5-b]pyridine,
19 - 1-{4-[4-(2-pyrimidinyl)-1-piperazinyl]butyl}-1H-benzotriazole,
20 - 2-chloro-1-{4-[4-(2-pyrimidinyl)-1-piperazinyl]-butyl}-1H-benzimidazole,
21 - 5-chloro-1-{4-[4-(2-pyrimidinyl)-1-piperazinyl]-butyl}-1H-benzimidazole,
22 - 6-chloro-1-{4-[4-(2-pyrimidinyl)-1-piperazinyl]-butyl}-1H-benzimidazole,
23 - 1-{4-[4-(2-pyrimidinyl)-1-piperazinyl]butyl}-1H-1,2,4-triazole,
24 - 2-{4-[4-(2-pyrimidinyl)-1-piperazinyl]butyl}-2H-benzotriazole,
25 - 2-methyl-1-{4-[4-(2-pyrimidinyl)-1-piperazinyl]-butyl}-1H-benzimidazole,
26 - 5,6-dimethyl-1-{4-[4-(2-pyrimidinyl)-1-piperazinyl]-butyl}-1H-benzimidazole,
27 - 1-{4-[4-(2-pyrimidinyl)-1-piperazinyl]butyl}-1H-pyrazole,
28 - 3,5-dimethyl-1-{4-[4-(2-pyrimidinyl)-1-piperazinyl]-butyl}-1H-pyrazole,
29 - 3,5-dimethyl-4-nitro-1-{4-[4-(2-pyrimidinyl)-1-piperazinyl]butyl}-1H-pyrazole,
30 - 4-methyl-1-{4-[4-(2-pyrimidinyl)-1-piperazinyl]-butyl}-1H-pyrazole
31 - 1-{4-[4-(2-pyrimidinyl)-1-piperazinyl]butyl}-1H-indazole,
32 - 4-bromo-3,5-dimethyl-1-{4-[4-(2-pyrimidinyl)-1-piperazinyl]butyl}-1H-pyrazole,
33 - 4-nitro-1-{4-[4-(2-pyrimidinyl)-1-piperazinyl]-butyl}-1H-pyrazole,
34 - 4-chloro-1-{4-[4-(2-pyrimidinyl)-1-piperazinyl]-butyl}-1H-pyrazole,
35 - ethyl 1-{4-[4-(2-pyrimidinyl)-1-piperazinyl]butyl}-1H-pyrazole-4-carboxylate,
36 - 3-methyl-5-phenyl-1-{4-[4-(2-pyrimidinyl)-1-piperazinyl]butyl}-1H-pyrazole, 37 - 4-bromo-1-{4-[4-(2-pyrimidinyl)-1-piperazinyl]-butyl}-1H-pyrazole,
38 - 4-cyano-1-{4-[4-(2-pyrimidinyl)-1-piperazinyl]-butyl}-1H-pyrazole,
39 - 4-fluoro-1-{4-[4-(2-pyrimidinyl)-1-piperazinyl]-butyl}-1H-pyrazole,
40 - 4-methoxy-1-{4-[4-(2-pyrimidinyl)-1-piperazinyl]-butyl}-1H-pyrazole,
41 - 4-amino-1-{4-[4-(2-pyrimidinyl)-1-piperazinyl]-butyl}-1H-pyrazole,
42 - 4-methylsulfonamido-1-{4-[4-(2-pyrimidinyl)-1-piperazinyl]butyl}-1H-pyrazole,
43 - 4-benzamido-1-{4-[4-(2-pyrimidinyl)-1-piperazinyl]-butyl}-1H-pyrazole,
44 - 4-acetamido-1-{4-[4-(2-pyrimidinyl)-1-piperazinyl]-butyl}-1H-pyrazole,
45 - 4-(2-butyl)amino-1-{4-[4-(2-pyrimidinyl)-1-piperazinyl]butyl}-1H-pyrazole,
46 - 5-methyl-1-{4-[4-(2-pyrimidinyl)-1-piperazinyl]-butyl}-1H-pyrazole,
47 - 3-methyl-1-{4-[4-(2-pyrimidinyl)-1-piperazinyl]-butyl}-1H-pyrazole,
48 - 4-bromo-5-methyl-1-{4-[4-(2-pyrimidinyl)-1-piperazinyl]butyl}-1H-pyrazole,
49 - 4-bromo-3-methyl-1-{4-[4-(2-pyrimidinyl)-1-piperazinyl]butyl}-1H-pyrazole,
50 - 1-{4-[4-(2-pyrimidinyl)-1-piperazinyl]butyl}-1H-4,5,6,7-tetrahydroindazole,
51 - 2-{4-[4-(2-pyrimidinyl)-1-piperazinyl]butyl}-1H-3,4,5,6-tetrahydroindazole,
52 - 5-methyl-4-phenyl-1-{4-[4-(2-pyrimidinyl)-1-piperazinyl]butyl}-1H-pyrazole,
53 - 3-methyl-4-phenyl-1-{4-[4-(2-pyrimidinyl)-1-piperazinyl]butyl}-1H-pyrazole,
54 - 3-chloro-4-fluoro-1-{4-[4-(2-pyrimidinyl)-1-piperazinyl]butyl}-1H-pyrazole,
55 - 3-chloro-4-methoxy-1-{4-[4-(2-pyrimidinyl)-1-piperazinyl]butyl}-1H-pyrazole,
56 - 4-(4-methoxyphenyl)-1-{4-[4-(2-pyrimidinyl)-1-piperazinyl]butyl}-1H-pyrazole,
57 - 4-(4-chlorophenyl)-1-{4-[4-(2-pyrimidinyl)-1-piperazinyl]butyl}-1H-pyrazole,
58 - 4-(1-pyrrolyl)-1-{4-[4-(2-pyrimidinyl)-1-piperazinyl]butyl}-1H-pyrazole,
59 - 4-phenyl-1-{4-[4-(2-pyrimidinyl)-1-piperazinyl]-butyl}-1H-pyrazole,
60 - 3,5-diphenyl-1-{4-[4-(2-pyrimidinyl)-1-piperazinyl]-butyl}-1H-pyrazole,
61 - 4-phenylsulfamoyl-1-{4-[4-(2-pyrimidinyl)-1-piperazinyl]butyl}-1H-pyrazole,
62 - 4-(4-methylbenzene)sulfamoyl-1-{4-[4-(2-pyrimidinyl)-1-piperazinyl]butyl}-1H-pyrazole,
63 - 4-butylsulfamoyl-1-{4-[4-(2-pyrimidinyl)-1-piperazinyl]butyl}-1H-pyrazole,
64 - 4-propylsulfamoyl-1-{4-[4-(2-pyrimidinyl)-1-piperazinyl]butyl}-1H-pyrazole,
65 - 4-ethylsulfamoyl-1-{4-[4-(2-pyrimidinyl)-1-piperazinyl]butyl}-1H-pyrazole,
66 - 3,5-dimethyl-4-(N,N-dimethylsulfonamido)-1-{4-[4-(2-pyrimidinyl)-1-piperazinyl]butyl}-1H-pyrazole,
67 - 4-N-methylsulfamoyl-1-{4-[4-(2-pyrimidinyl)-1-piperazinyl]butyl}-1H-pyrazole,
68 - 1-{4-[4-(2-pyrimidinyl)-1-piperazinyl]butyl}-1H-pyrazole-4-sulfonic,
69 - 1-{4-[4-(2-pyrimidinyl)-1-piperazinyl]butyl}-1H-imidazole.
70 - 2-methyl-1-{4-[4-(2-pyrimidinyl)-1-piperazinyl]-butyl}-1H-imidazole,
71 - 4,5-chloro-1-{4-[4-(2-pyrimidinyl)-1-piperazinyl]-butyl}-1H-imidazole,
72 - 4-methyl-1-{4-[4-(2-pyrimidinyl)-1-piperazinyl]-butyl}-1H-imidazole,
73 - 5-methyl-1-{4-[4-(2-pyrimidinyl)-1-piperazinyl]-butyl}-1H-imidazole,
74 - 4-chloro-1-{4-[4-(4-methoxyphenyl)-1-piperazinyl]-butyl}-1H-pyrazole,
75 - 4,5-dichloro-2-methyl-1-{4-[4-(4-methoxyphenyl)-1-piperazinyl]butyl}-1H-imidazole,
76 - 4-chloro-1-{4-[4-(2-methoxyphenyl)-1-piperazinyl]-butyl}-1H-pyrazole,
77 - 4,5-dichloro-2-methyl-1-{4-[4-(2-methoxyphenyl)-1-piperazinyl]butyl}-1H-imidazole,
78 - 4-chloro-1-{4-[4-(3-methoxhenyl)-1-piperazinyl]-butyl}-1H-pyrazole,
79 - 1-{4-[4-(4-methoxyphenyl)-1-piperazinyl]butyl}-pyrrole,
80 - 1-{4-[4-(2-methoxyphenyl)-1-piperazinyl]butyl}-pyrrole,
81 - 1-{4-[4-(phenyl)-1-piperazinyl]butyl}pyrrole,
82 - 4-chloro-1-{4-[4-(phenyl)-1-piperazinyl]butyl}-1H-pyrazole,
83 - 4,5-dichloro-2-methyl-1-{4-[4-(phenyl}-1-piperazinyl]butyl}-1H-imidazole,
84 - 4-chloro-1-{4-[4-(2-chlorophenyl)-1-piperazinyl]-butyl}-1H-pyrazole,
85 - 4,5-dichloro-2-methyl-1-{4-[4-(2-chlorophenyl)-1-piperazinyl]butyl}-1H-imidazole,
86 - 4-chloro-1-{4-[4-(3-chlorophenyl)-1-piperazinyl]-butyl}-1H-imidazole,
87 - 1-{4-[4-(2-N-methylimidazolyl)-1-piperazinyl]-butyl}-1H-pyrazole,
88 - 4-chloro-1-{4-[4-(1,2-benzisothiazol-3-yl)-1-piperazinyl]butyl}-1H-pyrazole,
89 - 4,5-dichloro-2-methyl-1-{4-[4-(1,2-benzisothiazol-3-yl)-1-piperazinyl]butyl}-1H-imidazole,
90 - 4-bromo-1-{4-[4-(5-bromopyrimidin-2-yl)-1-piperazinyl]butyl}-1H-pyrazole,
91 - 4-bromo-1-{4-[4-(5-chloropyrimidin-2-yl)-1-piperazinyl]butyl}-1H-pyrazole,
92 - 2-methyl-1-{4-[4-(2-pyrimidinyl)-1-piperazinyl]-butyl}-1H-imidazole.

9. The process of claim 2 wherein said solvent is selected from the group consisting of heptane, benzene, toluene, dioxane and diphenyl ether.

10. The process of claim 4 wherein said base is an organic base of the group consisting of pyridine, triethylamine or potassium tert-butoxide.

11. The process of claim 7 wherein said temperature in between about 80° C. and 160° C.

* * * * *

UNITED STATES PATENT AND TRADEMARK OFFICE
CERTIFICATE OF CORRECTION

PATENT NO. : 5,227,486  Page 1 of 4
DATED : July 13, 1993
INVENTOR(S) : Ramon Merce-Vidal et al.

It is certified that error appears in the above-indentified patent and that said Letters Patent is hereby corrected as shown below:

In the ABSTRACT, at column 2 of the title page, before the chemical formula IX and after the word "wherein", insert the phrase --a compound of the general formula IX--.

In column 1, at line 21, before the symbol "$Z_1$", insert the phrase --Ar denotes a nitrogenous or other aromatic radical chosen from differently substituted aryls, differently substituted 2-pyrimidine, 2-N-methyl-imidazole and 3-(1,2-benzisothiazole)--.

In column 1, at line 55, after the word "formula", insert --II--.

In column 3, at line 1, in the chemical formula IX, delete "$N^-$" and replace it with --$N^+$--.

In TABLE I, Example 2, delete "C-CH=CH-CH=CH-" and replace it with --C-CH=CH-CH=CH-C--; and in the IR $cm^{-1}$ column of the table, delete the number "1585" and replace it with the number --1586--.

In TABLE I, Example 3, in the IR $cm^{-1}$ column of the table, after the number "1585" add the following: --1547, 1510, 1446, 1359, 1259, 983, 741 (film)--; and in the column of the table labeled $^1$H-NMR, delete the number "2.79" and replace it with --3.79--.

UNITED STATES PATENT AND TRADEMARK OFFICE
CERTIFICATE OF CORRECTION

PATENT NO. : 5,227,486
DATED : July 13, 1993
INVENTOR(S) : Ramon Merce-Vidal et al.

It is certified that error appears in the above-indentified patent and that said Letters Patent is hereby corrected as shown below:

In TABLE I, Example 4, in the $^1$H-NMR column of the table, delete "2H); 6.41" and replace it with --4H); 4.11--.

In TABLE I, Example 5, in the $^1$H-NMR column of the table, between the lines "(broad, 1H); 7.89(S, 1H);" and "(d, J=4.6Hz, 2H)" insert the line --8.24 (s, 1H); 8.35--.

In TABLE I, Example 11, delete the number "2.7", and replace it with the number --2.57--.

In TABLE I, Example 21 and Example 22, in the column of the table labeled $R_3$, the letter "N" should be moved to the next column to the right and the entry in that column shifted one column to the right and so on.

In TABLE I, Example 25, in the $Z_2$ colummn of the table, please add the letter --N--.

In TABLE I, Example 27, in the $^1$H-NMR column of the table, delete the number "1.5" and replace it with --1.6--.

UNITED STATES PATENT AND TRADEMARK OFFICE
CERTIFICATE OF CORRECTION

PATENT NO. : 5,227,486
DATED : July 13, 1993
INVENTOR(S) : Ramon Merce-Vidal et al.

It is certified that error appears in the above-indentified patent and that said Letters Patent is hereby corrected as shown below:

In TABLE I, Example 50, in the IR $cm^{-1}$ column of the table, after the number "1590" add the following" --1550, 1500, 1450, 1360, 1310, 1260, 980 (film)--; and in the $^1$H-NMR column after "(m, 10H);" add the following: --3.8 (m, 4H); 4.04 (t, 2H, J=6.9); 6.43 (t, 1H, J=4.7); 7.23 (d, 1H, J=1.8); 8.26 (d, 2H, J=4.7)--.

In TABLE I, Example 56, in the IR $cm^{-1}$ column of the table, delete the number "833" and replace it with --835--; and in the $^1$H-NMR column of the table, delete "3-4.7" and replace it with --J=4.7--.

In TABLE I, Example 57, in the $R_3$ column of the table, delete the "o" from the chemical structure and replace it with --Cl--.

UNITED STATES PATENT AND TRADEMARK OFFICE
CERTIFICATE OF CORRECTION

PATENT NO. : 5,227,486
DATED : July 13, 1993
INVENTOR(S) : Ramon Merce-Vidal et al.

It is certified that error appears in the above-indentified patent and that said Letters Patent is hereby corrected as shown below:

In column 32, line 2, claim 8, delete the phrase "(4-(4-[4-(2-pyrimidinyl)" in the name of the compound and replace it with --{4-[4-(2-pyrimidinyl)--.

In column 32, lines 29 and 31, delete the letter "b" and replace it with --b--.

Signed and Sealed this

Fifth Day of July, 1994

BRUCE LEHMAN

Attest:

Attesting Officer

Commissioner of Patents and Trademarks